United States Patent
Parr et al.

(10) Patent No.: US 12,226,318 B2
(45) Date of Patent: Feb. 18, 2025

(54) IMPLANTABLE MEDICAL DEVICE

(71) Applicant: 3DMORPHIC PTY LTD, Matraville (AU)

(72) Inventors: William Chase Harrington Parr, Tamarama (AU); Ralph Jasper Mobbs, Coogee (AU)

(73) Assignee: 3DMORPHIC PTY LTD, Matraville (AU)

( * ) Notice: Subject to any disclaimer, the term of this patent is extended or adjusted under 35 U.S.C. 154(b) by 412 days.

(21) Appl. No.: 17/311,252

(22) PCT Filed: Dec. 5, 2019

(86) PCT No.: PCT/AU2019/051332
§ 371 (c)(1),
(2) Date: Jun. 4, 2021

(87) PCT Pub. No.: WO2020/113276
PCT Pub. Date: Jun. 11, 2020

(65) Prior Publication Data
US 2022/0015918 A1    Jan. 20, 2022

(30) Foreign Application Priority Data
Dec. 6, 2018 (AU) .................... 2018904650

(51) Int. Cl.
*A61F 2/44* (2006.01)
*A61F 2/30* (2006.01)
(52) U.S. Cl.
CPC .......... *A61F 2/442* (2013.01); *A61F 2/30771* (2013.01); *A61F 2/30942* (2013.01);
(Continued)

(58) Field of Classification Search
CPC .......... A61F 2/44; A61F 2/442; A61F 2/4455; A61F 2/30; A61F 2/30771; A61F 2/30942
See application file for complete search history.

(56) References Cited

U.S. PATENT DOCUMENTS

| 5,514,180 A | 5/1996 | Heggeness et al. |
| 6,890,355 B2 | 5/2005 | Michelson |

(Continued)

FOREIGN PATENT DOCUMENTS

WO    WO-2019145810 A1    8/2019

OTHER PUBLICATIONS

EP Application No. 19893543.9, Extended European Search Report dated Dec. 9, 2021, 8 pages.
(Continued)

*Primary Examiner* — Christopher J Beccia
(74) *Attorney, Agent, or Firm* — Cooley LLP

(57) ABSTRACT

A component including: a body having one or more surfaces with a contour formed to be substantially complementary to an anatomical surface of a specific patient; the body adapted to securably engage with a component-engaging part to form at least part of an implantable medical device, wherein: the one or more surfaces are substantially configured to evenly engage with the anatomical surface of the specific patient when the component is secured to the component-engaging part and the medical device implanted in the patient; and the body is at least in part manufactured by additive manufacturing.

25 Claims, 11 Drawing Sheets

(52) U.S. Cl.
CPC .. *A61F 2/4455* (2013.01); *A61F 2002/30593* (2013.01); *A61F 2002/30841* (2013.01); *A61F 2002/30948* (2013.01); *A61F 2002/30985* (2013.01)

(56) References Cited

U.S. PATENT DOCUMENTS

| | | |
|---|---|---|
| 8,353,964 B2 | 1/2013 | Carpenter |
| 2006/0282020 A1* | 12/2006 | Bertagnoli ............... A61F 2/44 700/118 |
| 2007/0043442 A1 | 2/2007 | Abernathie et al. |
| 2008/0046090 A1 | 2/2008 | Paul et al. |
| 2010/0240012 A1* | 9/2010 | Lange ................. A61C 8/0051 433/201.1 |
| 2012/0209384 A1 | 8/2012 | Arnold et al. |
| 2012/0312778 A1 | 12/2012 | Ullrich, Jr. et al. |
| 2016/0270931 A1* | 9/2016 | Trieu .................... A61F 2/4637 |
| 2018/0098861 A1 | 4/2018 | Howard et al. |
| 2018/0256336 A1 | 9/2018 | Mueller et al. |

OTHER PUBLICATIONS

PCT Application No. PCT/AU2019/051332, International Preliminary Report on Patentability dated Apr. 6, 2021, 7 pages.
PCT Application No. PCT/AU2019/051332, International Search Report and Written Opinion mailed Feb. 17, 2020, 17 pages.
Office Action for EP Application No. 19893543.9, by 3DMORPHIC PTY LTD, mailed Nov. 21, 2024; 4 pages.

* cited by examiner

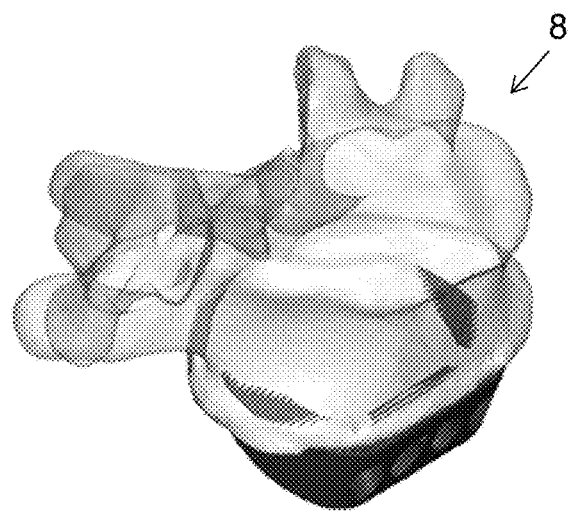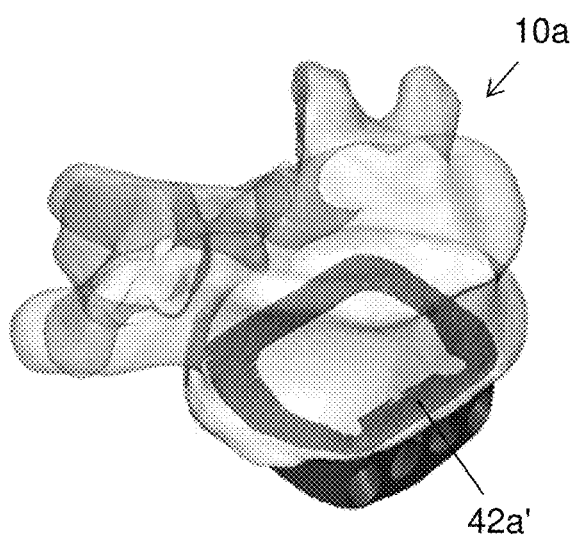
Figure 3          Figure 4
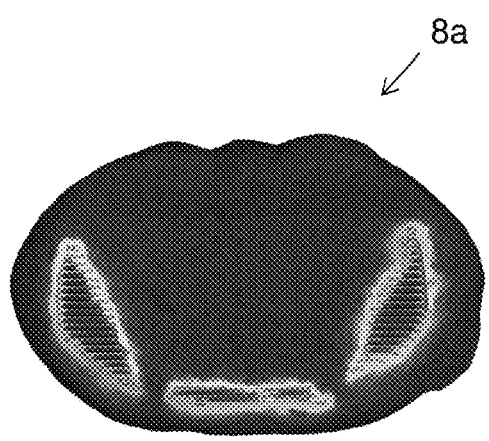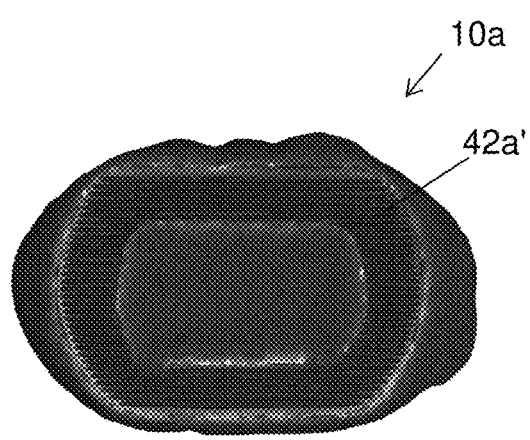
Figure 5

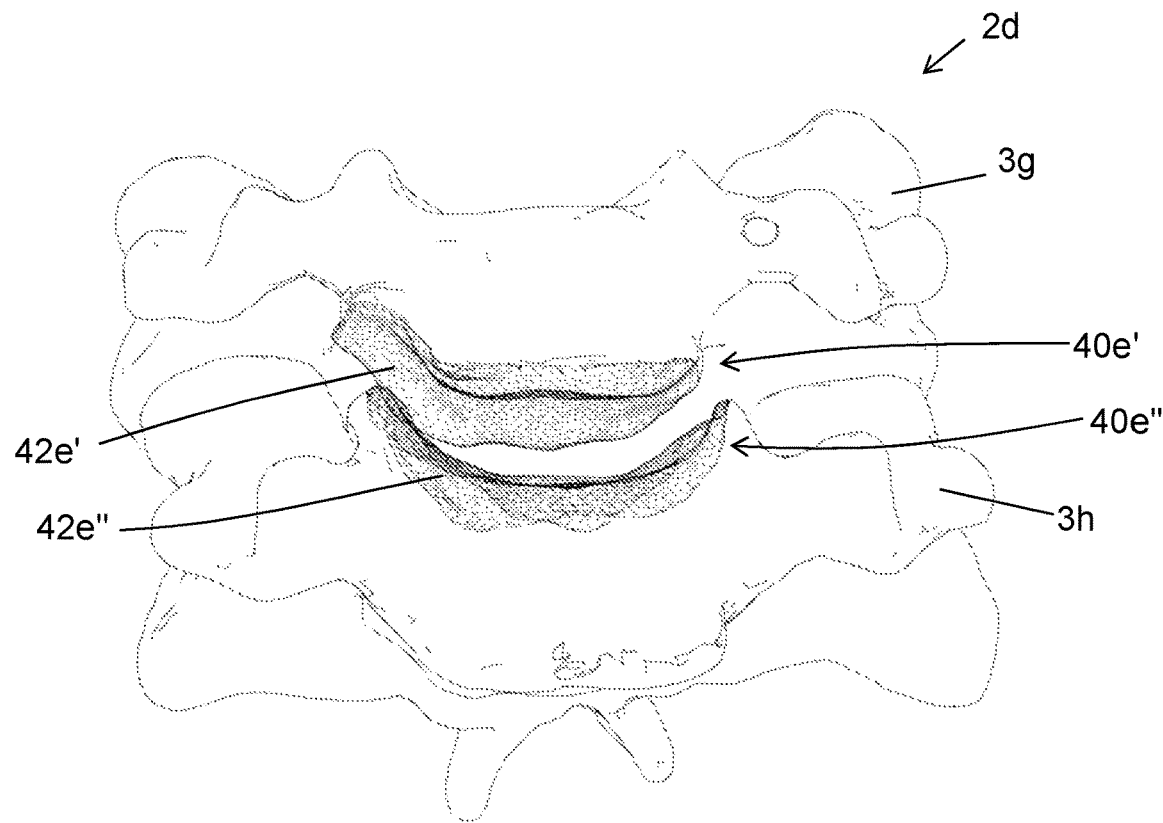
Figure 14
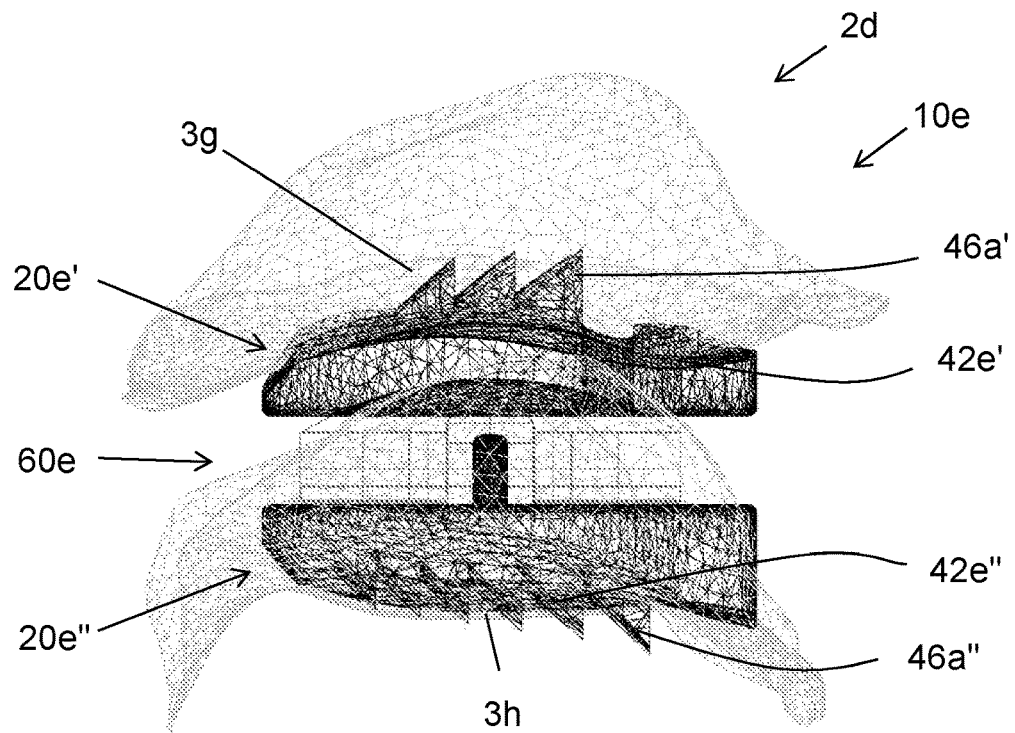
Figure 15 – disc replacement device

IMPLANTABLE MEDICAL DEVICE

CROSS REFERENCE TO RELATED APPLICATION

This application is a U.S. National Phase application, filed under 35 U.S.C. § 371, of International Application No. PCT/AU2019/051332, filed on Dec. 5, 2019, which claims priority to Australian Provisional Patent Application No 2018904650 filed 6 Dec. 2018, the contents of each of which are incorporated herein by reference in its entirety.

FIELD OF THE INVENTION

The invention relates to an implantable medical device. In particular, the invention relates, but is not limited, to a customised implantable medical device as well as a method associated with the device.

BACKGROUND TO THE INVENTION

Reference to background art herein is not to be construed as an admission that such art constitutes common general knowledge in Australia or elsewhere.

Reducing medical procedure times assists with, amongst other things, reducing risk of patient infection and the cost of procedures. It also allows hospital resources to be more effectively managed. In order to reduce medical procedure times, devices have been designed to generally fit with patient anatomy. By way of example, there has been a move within the medical device field towards altering mass-produced generic design parameters so that these mass-produced generic, off-the-shelf (OTS) devices better fit the majority of patient anatomies. In other cases, completely new mass-produced generic designs for anatomy fitting OTS devices are created, sometimes termed anatomical designs.

With the above cases, the designs are generic, mass produced and held in storage—either in the hospitals where they will be used, or by the device manufacturers so that they can be dispatched to meet hospital demand. Whilst this system is intended to minimise wait time for patient treatment caused by the logistics of getting a suitable device to the operating theatre, these devices may require manual modifications during surgery, or conversely the patient's anatomy may require surgical modification to enable the device to fit, increasing operating times (as outlined further below).

Another approach of medical devices fitting the patient is to measure and design a 'bespoke' personalised (custom-made, patient specific, customised) device specifically for an individual patient. Frequently these devices are designed from medical imaging of the patient (X-Ray, Computed Tomography (CT), Magnetic Resonance Imaging (MRI)), or from 3D reconstructions made from imaging. These 3D reconstructions can be volumetric renders or, more likely, 3D iso-surface (boundary representation) reconstructions made from segmentation of the Digital Imaging and Communications in Medicine (DICOM) image stacks acquired from medical imaging. In such cases, anatomical regions of interest are identified, either manually or automatically (for example, by greyscale value or Hounsfield unit), throughout the stack and segmented, where segmentation is effectively the binarisation of each image in the stack into regions to keep and regions to discard.

When segmentation is automated via grey scale (or Hounsfield unit) boundaries, the outline of these regions in each stack is defined as the change of greyscale to above/below a threshold. This means that the boundary of each region will have the same (iso) threshold value in much the same way that iso-bars on a weather pressure system map trace the outline of regions in the atmosphere. 3D surface reconstruction is achieved through interpolation of the boundaries between adjacent slices in the image stack. As the boundaries have the same (iso) threshold values, these types of 3D reconstruction are termed iso-surface boundary representations. Algorithms such as the 'marching cubes algorithm', modifications and derivations of this algorithm have been shown to create accurate (precise and true) reconstructions of the anatomy that was imaged.

Such devices can be manufactured by Computer Aided Manufacturing (CAM) methods such as Computer Numerical Control (CNC) machine milling or three-dimensional Printing (3DP), also known as Additive Manufacturing (AM) and Rapid Prototyping (RP).

The workflow for such customised devices when manufactured using 3DP frequently resembles guidelines taken from the United States of America (US) Federal Drug Administration (FDA) 2017 documentation 'Technical Considerations for Additive Manufactured Medical Devices'. The first step is the design process, which can include a standard design with discrete pre-specified sizes and models, or a patient-matched device designed from a patient's own medical images. Once the device design is converted to a digital file, the software workflow phase begins, and that file is further processed to prepare it for printing. Printing parameters are typically optimized, and the build file is converted into a machine-ready format. Concurrently with this step, material controls are normally established for materials used in the printing of the device. After printing is complete, post-processing of the built device or component (e.g., cleaning, annealing, post-printing machining, surface chemical treatment, sterilization, packing and labelling) takes place. After post-processing, the final finished device is ready for testing and characterization.

3DP is a manufacturing method for producing personalised medical devices whereby the cost of a device is largely dependent on the volume of material in the device. By way of example, for designs where the volume of material in the device is the same, the cost of manufacturing new personalised device designs via 3DP is reduced compared to the cost of manufacturing via existing mass-produced methods (e.g. milling, turning etc.).

This is not true for other mass production methods of manufacturing such as moulding and casting. For these more 'traditional' mass production methods, there is substantial set up time and cost involved in creating a new tool pathway or mould, with individual device units becoming economical, and cheaper than those produced by 3DP, only when many multiples of the exact same device are produced from the same tool path or mould—the 'economy of scale'. In such cases the cost of production for an individual mass-produced generic device unit is lower than if the same design were produced via 3DP. However, 3DP has the advantage of allowing further design freedom whereby complex geometries can be manufactured that are not possible to manufacture through traditional means, such as internal geometries and varied lattice topologies.

3DP is therefore a potential choice for producing personalised medical devices that are designed to fit a specific patient from medical imaging data taken from the patient. That being said, the machine manufacturing stage of the overall production of the 3DP device is only one out of 5 major parts of the overall workflow described above. As the cost of a device manufactured through 3DP is proportional to the volume of the device, the use of 3DP to manufacture complete large volume personalised medical devices can result in each device (unit) being relatively expensive. There are also space limitations in the 'build volume' of the 3DP machines, so devices with a larger build platform footprint mean that fewer devices can be packed onto the build platform and built simultaneously.

Furthermore, having to maintain a 3D printing machine for more build cycles, where fewer devices are produced per cycle, can increase the cost of each device unit further. This increase in cost for increased build cycles can come from technician hours spent setting up each build cycle, or, for example, maintaining 'Material Control' of the build material (powder, resin, polymer etc) to the required standard.

A recent report detailed the use of a personalised cervical corpectomy implant designed from pre-operative scan data where 32 implant units of differing dimensions (height and widths) were supplied to the Operating Theatre (OT) to ensure that one device would fit intra-operatively. The surgery was reportedly a success, with one of the devices fitting well into the surgically created space between Cervical vertebra one (C1) and C5, but the remaining 31 personalised implant units were effectively waste. The material from these units can be recycled, but this is a costly process in itself.

Additionally, designing, manufacturing, post-processing, cleaning and packaging of extra devices means that procedures utilising such personalised methods quickly becomes costly so as to be reserved for only the most extreme cases. Further, health care providers and insurers are likely to be highly resistant to the implementation of such procedures as routine due to cost burdens associated therewith, even if the patient outcome is demonstrably better compared to using a non-personalised, mass-produced generic, OTS device.

One particular area that personalised devices benefit patient, surgeon, health care providers (hospitals) and insurers is that personalised devices are often very rapid to implant as less preparation of the (bony) anatomy is needed to accommodate the device. With mass-produced generic devices (e.g. spinal interbody devices such as spacers and corpectomy cages), it is usually necessary for the surgeon to prepare the anatomy, for instance by rasping or burring away bone lumps and bumps, in order to either get the mass-produced generic device to fit into the anatomical space, or to improve the contact between the anatomy and device interface by matching the anatomical morphology to the device geometry. Such surgical preparation can be time consuming, and necessarily increases trauma to the patient. Time savings can be considerable, in the order of 45 minutes-1 hour for complex anatomy. These time savings also decrease the costs associated with surgery as less resources are required including surgeon time.

With the above in mind, complex surgical cases, which are typical of cancer resection cases, can take many hours (~8 hrs would not be un-common). Interbody (e.g. corpectomy) devices are typically implanted towards the end of the surgical procedure, by which time the patient may have lost considerable amounts of blood. Cooling of the operating room is also standard practice. In such cases, an additional 45 minutes-1 hour added to the end of the procedure due to the surgeons having to prepare the patient anatomy to accommodate a poorly fitting mass-produced generic device can make a real difference. In particular, i) there are increased risks (e.g. risk of stroke) associated keeping a patient anaesthetised for prolonged periods of time; ii) blood loss may be sufficient to either jeopardise critical organ function or necessitate an (emergency) intra or post-operative blood transfusion; iii) increases in the time that a wound remains open increases the risk of an infection occurring in the wound post-operatively; and iv) the patient's core temperature will drop leaving the patient at risk of hypothermia.

Thus, there are demonstrable cost and patient draw-backs for the devices under current design and manufacturing workflows and practices.

SUMMARY OF INVENTION

In one aspect, the invention resides in a component including:
  a body having one or more surfaces with a contour formed to be substantially complementary to an anatomical surface of a specific patient;
  the body adapted to securably engage with a component-engaging part to form at least part of an implantable medical device,
  wherein:
  the one or more surfaces are substantially configured to evenly engage with the anatomical surface of the specific patient when the component is secured to the component-engaging part and the medical device implanted in the patient; and
  the body is at least in part manufactured by additive manufacturing.

In an embodiment, the anatomical surface of the specific patient is retrieved from that patient prior to surgery.

In an embodiment, the anatomical surface of the specific patient is defined by one patient only.

In an embodiment, the anatomical surface of the specific patient is unique to that patient such that the one or more surfaces have been explicitly designed for the specific patient.

In an embodiment, the one or more surfaces are manufactured by additive manufacturing for the specific patient such that at least part of the one or more surfaces will not engage a different patient as evenly.

In an embodiment, the body is not manufactured to service multiple patients.

In an embodiment, additive manufacturing is in the form of 3D printing (also termed rapid prototyping).

In an embodiment, the anatomical surface is within the body of a human or animal patient.

In an embodiment, the anatomical surface is taken in-situ within the human or animal patient.

In an embodiment, the anatomical surface is a bone or joint surface.

In an embodiment, the bone or joint surface may be selected from a surface of a spinal vertebra, knee, hip or the like.

In an embodiment, the one or more surfaces are matched to be complementary to the anatomical surface by retrieving a scan of the anatomical surface of the specific patient.

In an embodiment, the one or more surfaces are substantially complementary to the anatomical surface by producing a complementary area based on a scan of the anatomical surface of the specific patient.

In an embodiment, the one or more surfaces are configured to align with the anatomical surface.

In an embodiment, a triangulated point (also termed triangulated vertex) surface definition is used to assist in defining the one or more surfaces. In an embodiment, the triangulated point (vertex) surface definition is different to a parametric Computer Aided Design (CAD) surface definition.

In an embodiment, the one or more surfaces include one or more curved surfaces.

In an embodiment, the body includes a part engaging surface.

In an embodiment, the part engaging surface is located on an opposite side of the body to the one or more surfaces.

In an embodiment, the part engaging surface maintains a connection with the component-engaging part.

In an embodiment, the part engaging surface is held in securable engagement with the component-engaging part through friction.

In an embodiment, the part engaging surface includes a first surface vertically offset from a second surface.

In an embodiment, the body includes one or more fastening portions that assist in releasably connecting the part thereto.

In an embodiment, the one or more fastening portions include a hole.

In an embodiment, the hole extends through the body from the surface to the part engaging surface.

In an embodiment, the part engaging surface includes a substantially flat portion.

In an embodiment, the component has a set of teeth to further securely engage with the anatomical surface.

In an embodiment, the one or more surfaces of the component further includes one or more teeth projecting away from the one or more surfaces so as to engage with the anatomical surface.

In an embodiment, the teeth puncture through the outer layer of the anatomical surface to further engage and secure the component to the anatomical surface.

In an embodiment, the implantable medical device may be a spacer, a disc replacement, an expandable cage, a generic cage, or any type of implantable device for correcting skeletal dysfunction.

In another form the invention resides in an implantable medical device including:
 a component having a body with one or more surfaces that have a contour that is substantially complementary to an anatomical surface of a specific patient; and
 a component-engaging part that is adapted to securably engage with the component,
 wherein:
 the one or more surfaces are substantially configured to evenly engage with the anatomical surface of the specific patient when the component is connected to the component-engaging part and the medical device implanted in the patient; and
 the body is at least in part manufactured by additive manufacturing.

In an embodiment, the component-engaging part is configured to be included in a number of patients whilst the component has been explicitly designed for a specific patient.

In an embodiment, the component engaging part is a generic part that is readily swappable between a number of patients.

In an embodiment, the component-engaging part is adapted to move from a connected position with the component to a released position.

In an embodiment, the component is secured to the component-engaging part through frictional contact.

In an embodiment, the component is secured to the component-engaging part with the assistance of an undulating surface.

In an embodiment, the component is secured to the component-engaging part with one or more fasteners. In an embodiment, the one or more fasteners are in the form of screws.

In an embodiment, the component is formed from a different material compared to the component-engaging part.

In an embodiment, the component-engaging part is adjustable.

In an embodiment, the component-engaging part is configured to adjust from a first position to a second position.

In an embodiment, adjusting from the first position to the second position includes moving at least part of the component-engaging part substantially in a linear direction. Alternatively or additionally in an embodiment, adjusting from the first position to the second position includes orientating the component-engaging part.

In an embodiment, the implantable medical device includes a further component having a body with one or more surfaces having a contour that is substantially complementary to an anatomical surface of the specific patient.

In an embodiment, the one or more surfaces of the further component are different to the one or more surfaces of the component.

In an embodiment, the further component is adapted to connect with the component-engaging part such that the components are situated on separate sides of the component-engaging part.

In another form the invention resides in a method for implanting a medical device, the method including the steps of:
 retrieving a component having a body with one or more surfaces that have a contour substantially complementary to an anatomical surface of a specific patient;
 securing the component to a component-engaging part to form at least part of a medical device; and
 implanting the medical device into the specific patient such that the one or more surfaces substantially engage with the anatomical surface of the specific patient,
 wherein the body is at least in part manufactured by additive manufacturing.

In an embodiment, the step of securing the component to the component-engaging part includes retrieving a number of component-engaging parts to determine which one would allow the one or more surfaces to substantially complement the anatomical surface of the specific patient.

In an embodiment, the step of securing the component to the component-engaging part includes retrieving a number of component engaging parts to determine a suitable arrangement.

In an embodiment, the step of retrieving the component includes retrieving a number of components to determine which one or more surfaces have a contour that is substantially complementary to the anatomical surface of the specific patient.

In an embodiment, the step of securing the component to the component-engaging part includes fastening the component to the component-engaging part.

In an embodiment, the step of implanting the component includes adjusting at least a portion of the component-engaging part, relatively to another portion of the component-engaging part, from a first position to a second position.

In an embodiment, the step of adjusting the portion includes orientating and/or moving in a separate direction.

An advantage of the present invention is that one component-engaging part of the implantable medical device can be suitable for use in a variety of different patients. The component allows bespoke treatment for each patient without the need to make a completely different implantable medical device for each patient.

Further features and advantages of the present invention will become apparent from the following detailed description.

BRIEF DESCRIPTION OF THE DRAWINGS

By way of example only, preferred embodiments of the invention will be described more fully hereinafter with reference to the accompanying figures, wherein:

FIG. 3 illustrates a perspective view of a generic ALIF interbody device engaging with a bone surface;

FIG. 4 illustrates a perspective view of the ALIF device, as shown in FIG. 1, engaging with a bone surface of a patient;

FIG. 5 illustrates a stress analysis of the generic ALIF interbody device, as shown in FIG. 3, in comparison to the ALIF device shown in FIG. 4;

FIG. 14 illustrates a front view of the planned postoperative bone and bone surface (triangulated) configuration for a component, according to an embodiment of the invention;

FIG. 15 illustrates a side view of the shape of an implantable medical device in the form of a (floating) disc replacement device, according to an embodiment of the invention;

DETAILED DESCRIPTION OF THE DRAWINGS

Figure 1:
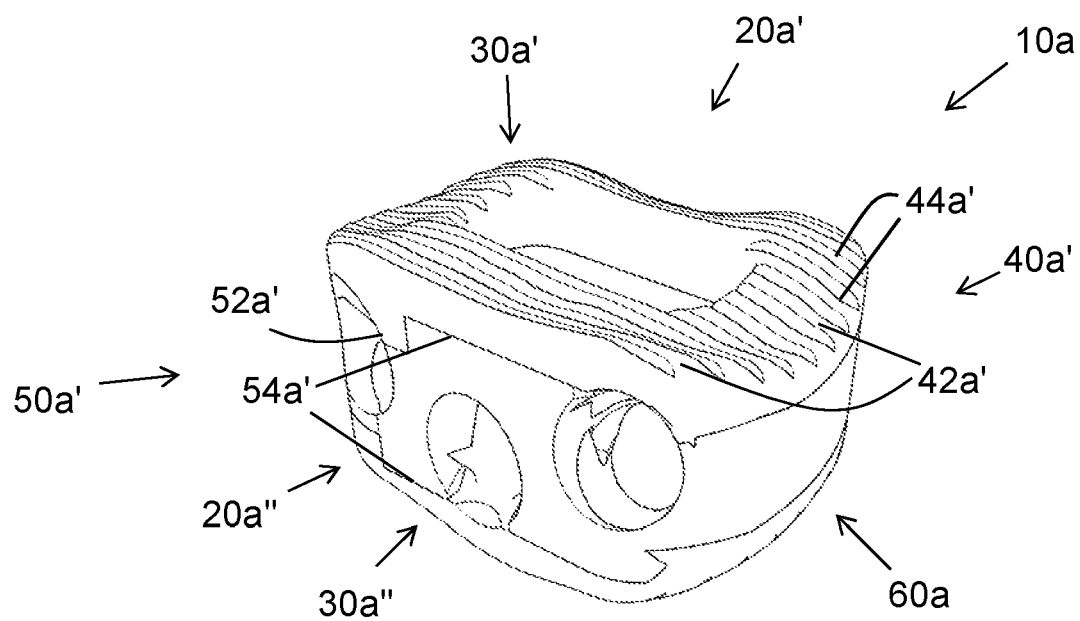
FIG. 1 illustrates a perspective view of an implantable medical device in the form of an anterior lumbar interbody fusion (ALIF) device, according to an embodiment of the invention.
Figure 2:
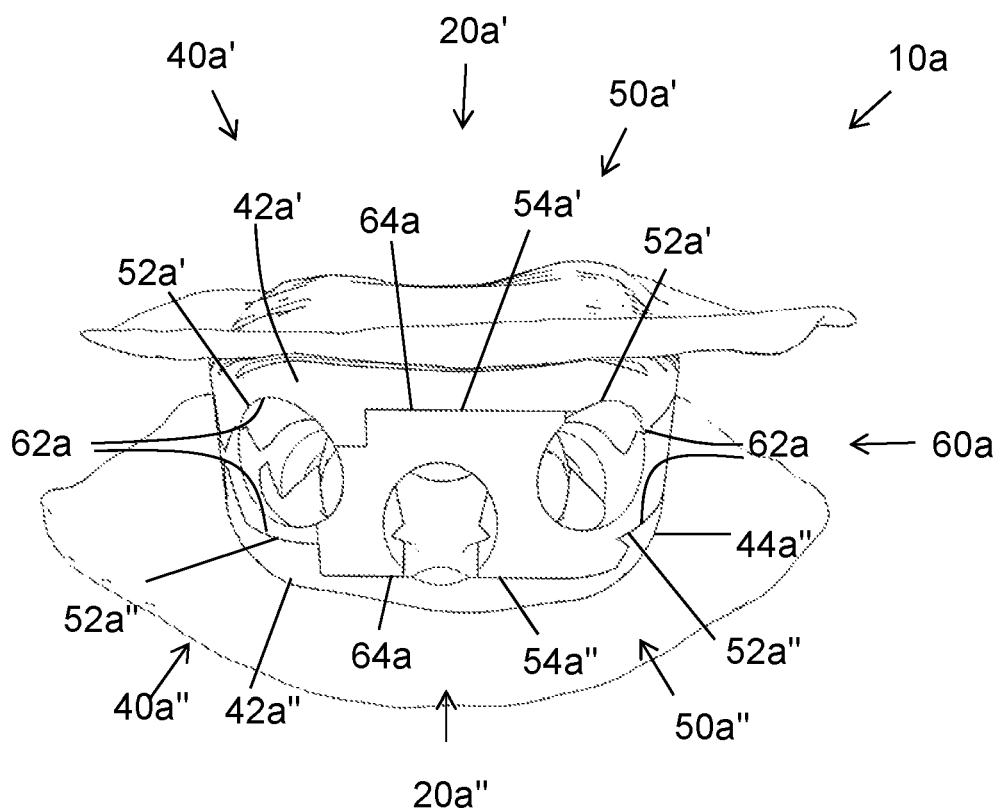
FIG. 2 illustrates a front view of the ALIF device, as shown in FIG. 1, engaging with a bone surface of a patient.

FIGS. 1 and 2 illustrate perspective and front views (respectively) of an implantable medical device 10a in the form of an ALIF device. In this regard, it is noted at the outset that the use of a reference numeral followed by a lower case letter and/or apostrophe in this specification typically indicates alternative embodiments of a general element identified by the reference numeral. Thus for example implantable medical device 10a is similar to but not identical to implantable medical device 10b. Further, references to an element identified only by the numeral refer to all embodiments of that element. Thus for example a reference to implantable medical device 10 is intended to include both the implantable medical device 10a and the implantable medical device 10b. In a similar manner, implantable medical device 10a could include implantable medical devices 10a' and 10a" (not shown).

The implantable medical device 10a includes two components 20a', 20a" each having a respective body 30a', 30a". The bodies 30a', 30a" have a number of surfaces 40a', 40a" each with a contour 42a', 42a" that are configured to be complimentary to an anatomical surface of a specific patient. That is, the contours 42a', 42a" have been design for a certain patient. They are not complimentary in the generic sense, they have been designed for one patient in mind only. In this embodiment, the contours 42a', 42a" are configured to substantially match surfaces of a spinal bone/joint surface which are typically non-linear. In this regard, the surfaces 40a', 40a" are different to each other to substantially match different areas of the bone/joint surface they engage with.

With the above in mind, the contours 42a', 42a" are defined by modelling a bone or joint surface of a patient (typically based on a scan of the anatomical surface). A triangulated point (vertex) surface definition may then be developed with the assistance of the scan. Following this, the bodies 30a', 30a" are typically printed through additive manufacturing (i.e. 3DP) to capture a suitable shape. In addition, the contours 42a', 42a" in this embodiment are also separated by apertures 44a', 44a". The apertures 44a', 44a" assist in providing some compliance between the components 20a', 20a" and the bone or joint surface. That is, the apertures 44a', 44a" assist in forming protrusions or teeth adjacent thereto that improve stability by providing better grip between the components 20a', 20a" and bone/joint surface. The apertures 44a', 44a" may take various forms. For example, in one or more embodiments the apertures 44a', 44a" may be a recessed region or a channel.

The components 20a', 20a" also each include a part engaging surface 50a', 50a". The part engaging surfaces 50a', 50a" are respectively on an opposite side of bodies 30a', 30a" in comparison to the surfaces 40a', 40a". Side surface(s) respectively separate the surfaces 40a', 40a" from the part engaging surfaces 50a', 50a". The part engaging surfaces 50a', 50a" each include a first engaging surface 52a', 52a" and a second engaging surface 54a', 54a". The first engaging surfaces 52a', 52a" are offset to the second engaging surfaces 54a', 54a". In particular, the second surface 54a', 54a" is located further away from the surfaces 40a', 40a" in comparison to the first engaging surface 52a', 52a". This assists in providing an undulating surface, with ledges, that allows the components 20a''', 20a'' to securely engage with a component-engaging part 60a (as discussed below).

The component-engaging part 60a in this embodiment is in the form of a generic part. That is, the component-engaging part 60a may be used amongst various patients and is used as a suitable spacer between the components 20a', 20a''. The component-engaging part 60a can therefore be swamped in and out, with other parts 60 of different sizes, to find a combination with components 20 that allows suitable engagement with the bone/joint surface. In this regard, the component-engaging part 60a includes a first engaging surface 62b and a second engaging surface 64b that respectively engage with the first engaging surfaces 52a', 52a'' and the second engaging surfaces 54b', 54b''. The engaging surfaces 52a', 52a'', 54b', 54b'', 62b, 64b are configured to interact to connect or secure the components 20a', 20a'' to the component-engaging part 60a.

FIG. 3 illustrates a traditional ALIF device 8a engaging with a bone surface whilst FIG. 4 illustrates the implantable medical device 10a. As shown in FIG. 3, the generically formed ALIF device 8a has a surface that does not substantially complement the bone surface. This is further evident from FIG. 5 illustrating a stress distribution of device 8a. In particular, stress hot spots, which can lead to device or anatomical structure failure, can be seen towards the front edges of bone engaging with device 8a due to its non-complimentary shape with the bone surface. In comparison, the implantable medical device 10a suitably matches the bone surface, decreasing stress hot spots, increasing even low magnitude stress distribution, as well as increasing contact surface area and stability of the device-anatomy construct.

Figure 6:
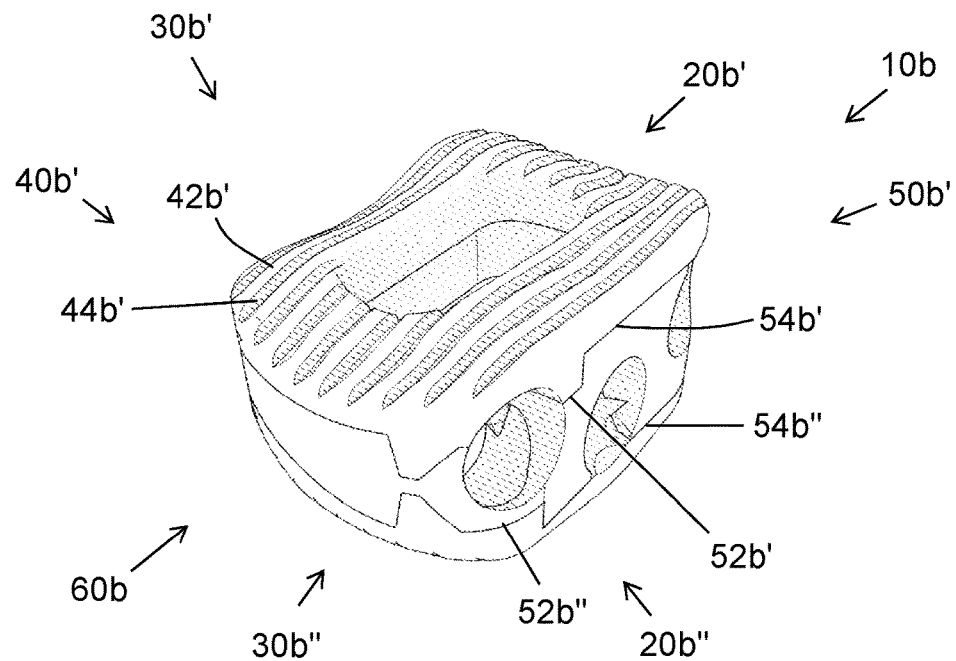
FIG. 6 illustrates a perspective view of a further implantable medical device in the form of a further ALIF device, according to another embodiment of the invention.
Figure 7:
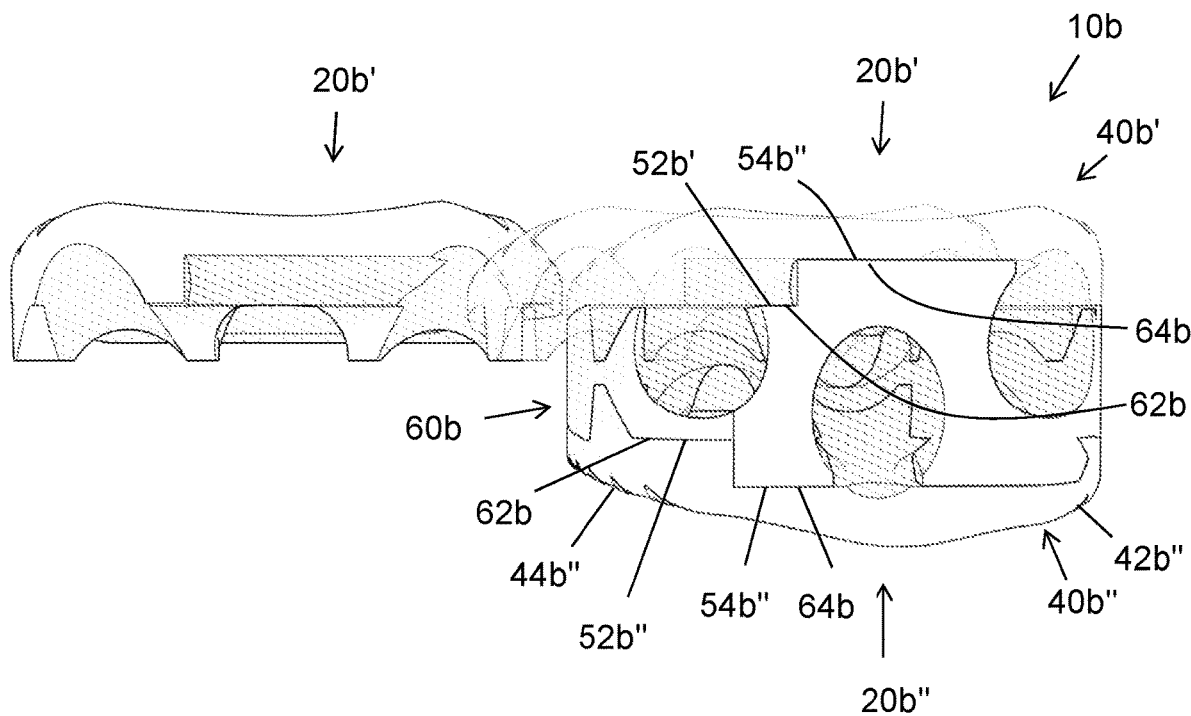
FIG. 7 illustrates replacing a component of the further ALIF device, according to an embodiment of the invention.

FIGS. 6 and 7 illustrate a further implantable medical device 10b in the form of an ALIF device. In a similar manner to the device 10a, the device 10b includes two components 20b', 20b'' located either side of a component-engaging part 60b. The components 20b', 20b'' each include a body 30b', 30b'' having surfaces 40b', 40b'' that are configured to be complementary to at least part of a bone or joint surface of a patient. The surfaces 40b', 40b'' include contours 42b', 42b'' that are non-linear in order to suitably engage the bone or joint surface. Furthermore, apertures 44b', 44b'' render gaps in surfaces 40b', 40b' that assist in forming protrusions or teeth adjacent thereto.

FIG. 7 further illustrates the interaction between the first surfaces 52b', 62b and the second surfaces 54b', 64b. In particular, the components 20b', 20b'' are configured to be slid into a secure engagement with the component-engaging part 60b. The geometry between the first surfaces 52b', 52b'', 62b and the second surfaces 54b', 54b'', 64b assists in creating a frictional engagement therebetween. Catches, lips and/or notches may also assist in connecting the components 20b', 20b'' to the component-engaging part 60b. In further embodiments, it would be appreciated that the components 20b', 20b'' may be secured to the component-engaging part 60b with, for example, one or more fasteners. In addition, it will also be appreciated that the sliding arrangement between the components 20b', 20b'' and the component-engaging part 60b allows the components 20b', 20b'' or part 60b to be readily replaced with different components/parts having a different size (i.e. height, angle etc.) or material.

Figure 8:
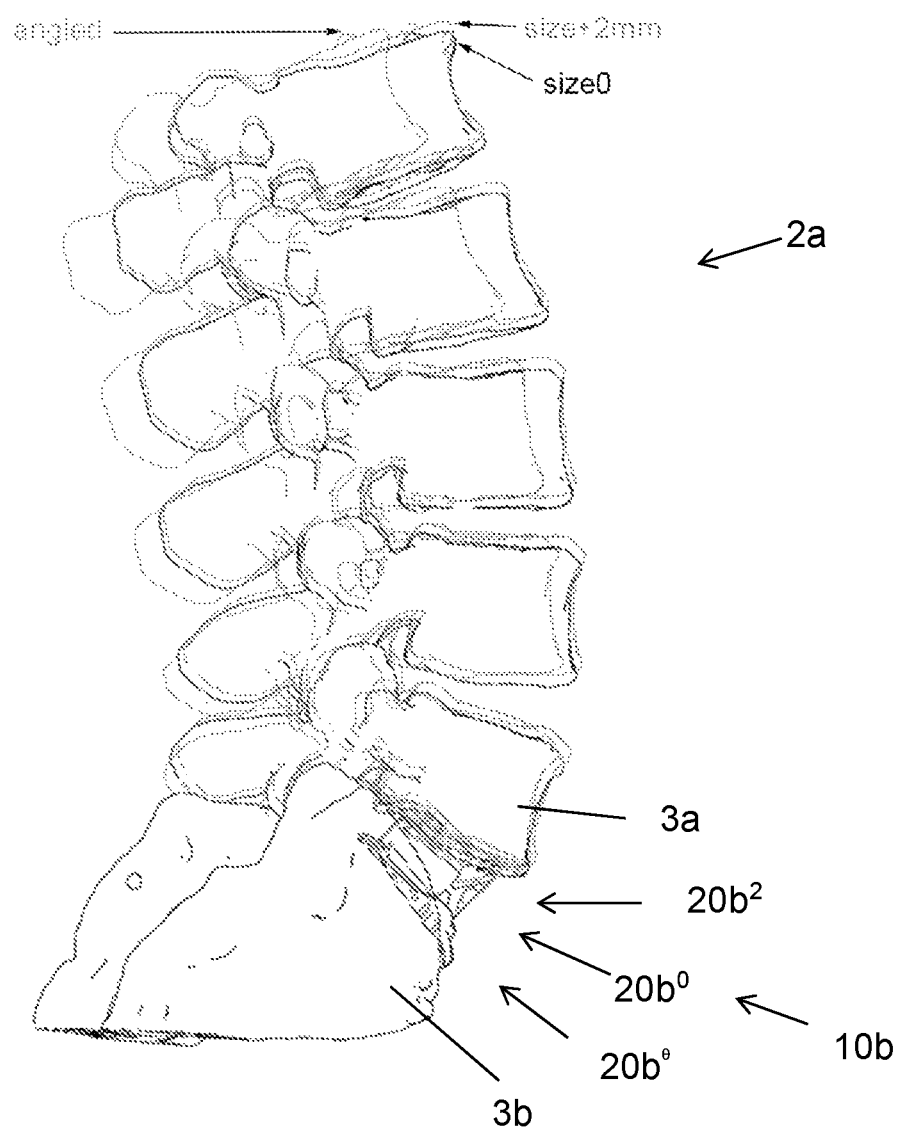
FIG. 8 illustrates a side view of spine adjustments associated with different component engaging parts of the further implantable medical device shown in FIGS. 6 and 7.

FIG. 8 illustrates the different positions of the spine 2a achieved through different height (termed size in FIG. 8) and angled components 20b located between vertebral bodies 3a, 3b. The +2 mm component $20b^2$ maintains the same superior spinal alignment as the 0 mm component $20b^0$ but the additional displacement may be desirable if there is a canal and/or foraminal stenosis compressing the neurological structures but the sagittal balance of the spine is suitable. The angled device $20b^\theta$ adjusts the sagittal balance of the spinal level, which may be desirable in cases where a collapsed disc has reduced the interbody, or disc space, lordotic angle. In this regard, FIG. 8 shows that when the lordotic angle of the disc space is reduced, the centre of mass of the spine, and the thorax, shifts anteriorly. An anterior shift in the centre of mass of the thorax leads to musclo-skeletal compensation throughout the thoracic and cervical spine and associated musculature, which can add to the clinical symptoms for the patient. On this basis, the components 20b can assist in finding a suitable compromise for this problem.

Figure 9:
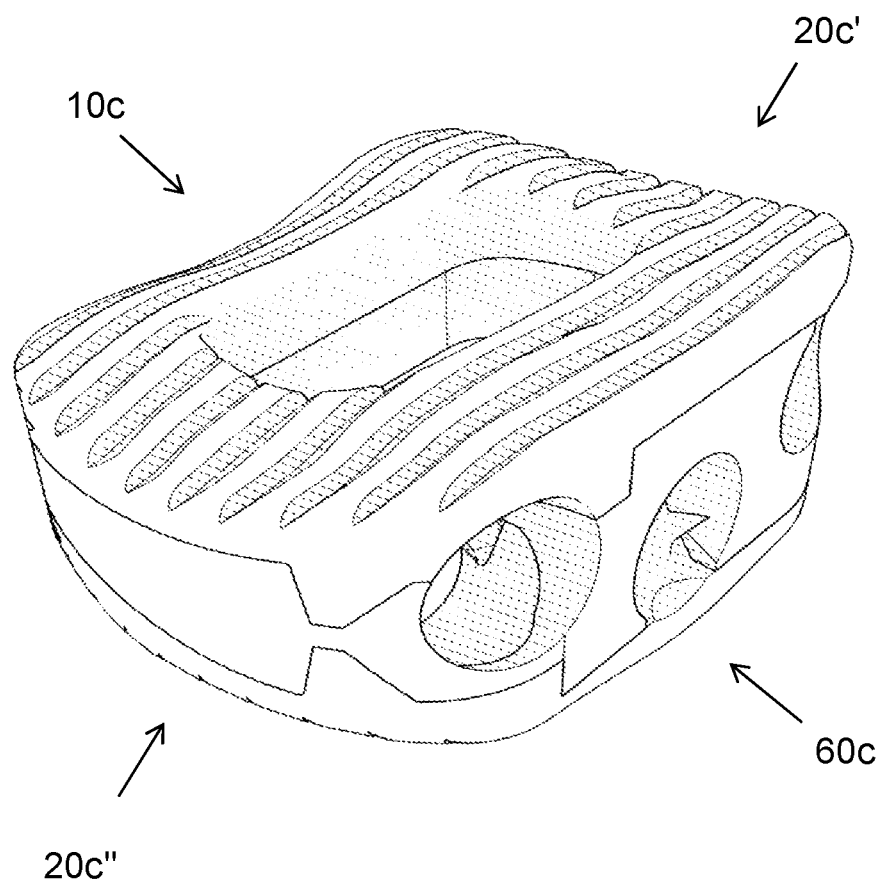
FIG. 9 illustrates a perspective view of an additional implantable medical device in the form of a separate ALIF device, according to another embodiment of the invention.

FIG. 9 illustrates a further implantable medical device 10c in the form of an ALIF device. The medical device 10c is substantially the same as device 10b but the overall height of 10c has been reduced compared to 10b by swapping generic middle part 60b for 60c. Components 20c', 20c'' are substantially the same as components 20b' and 20b'', respectively. In other words, and as evident from FIG. 8, FIG. 9 is further illustrating potential uses of the same components 20 with, for example, a different component-engaging part 60c.

Figure 10:
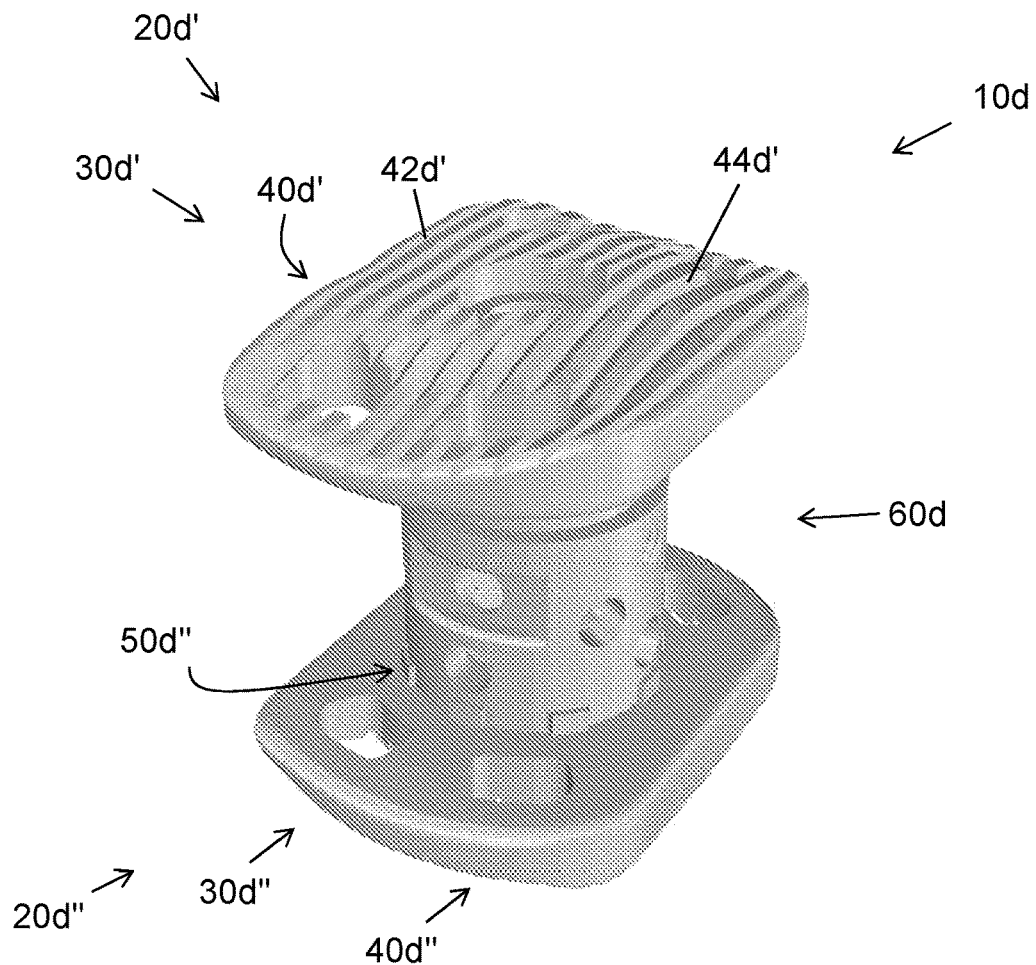
FIG. 10 illustrates a perspective view of an implantable medical device in the form of an expandable cage, according to an embodiment of the invention.

FIG. 10 illustrates an implantable medical device 10d in the form of an expandable cage. The device 10d includes two components 20d', 20d'', acting as endplates, on either end of a component-engaging part 60d. The components 20d', 20d'' each have a body 30d', 30d'' with respective surfaces 40d', 40d''. Component 20d' is shown further in FIG. 11. In this regard, it is noted that the surface 40d' has a contour 42d' that is somewhat convex in some regions, and somewhat concave in other regions. Furthermore, apertures 44d' in the form of channels separate the contours 42d' in order to assist with securing the component 20d' with the bone or joint surface.

Figure 11:
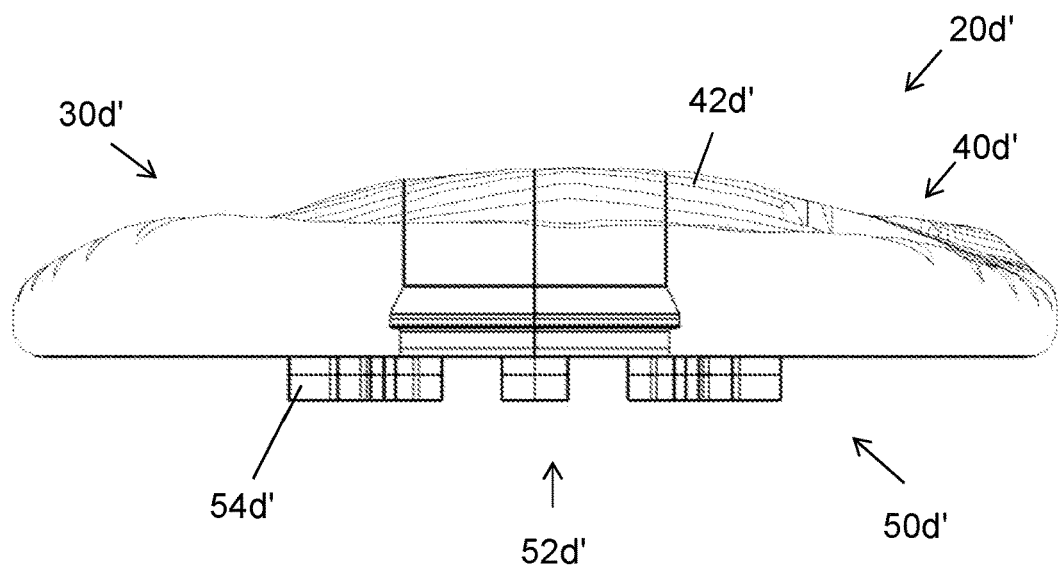
FIG. 11 illustrates a front view of a component of the expandable cage, shown in FIG. 10, according to an embodiment of the invention.

The components 20d', 20d'' include part engaging surfaces 50d', 50d''. As shown in FIG. 11, the part engaging surfaces 50d include a plurality of first engaging surfaces 52d' in the form of a number of protrusions. The protrusions extend from a substantially linear surface and away from the surface 40d'. The protrusions are configured to engage with the component-engaging part 60d in order to assist in securely connecting thereto. In particular, the protrusions form part of a click-in mechanism, including a click-in lip, and the protrusions prevent rotation about the component-engaging part 60d.

Figure 12:
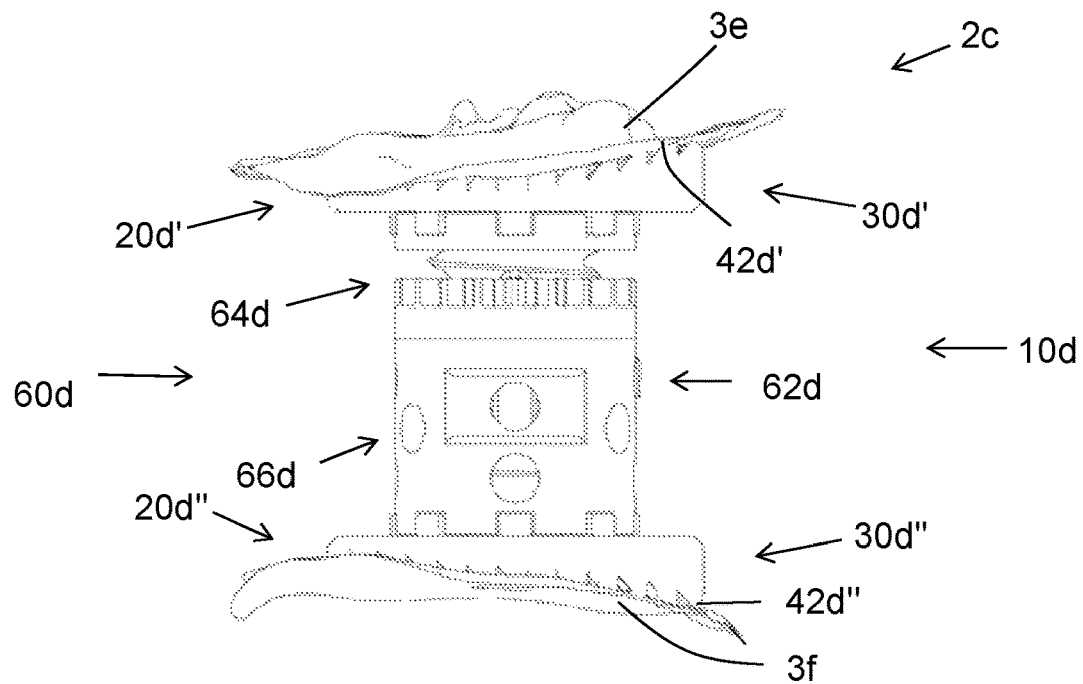
FIG. 12 illustrates a side view of the expandable cage, shown in FIG. 10, engaging with the bone surfaces of a patient.
Figure 13:
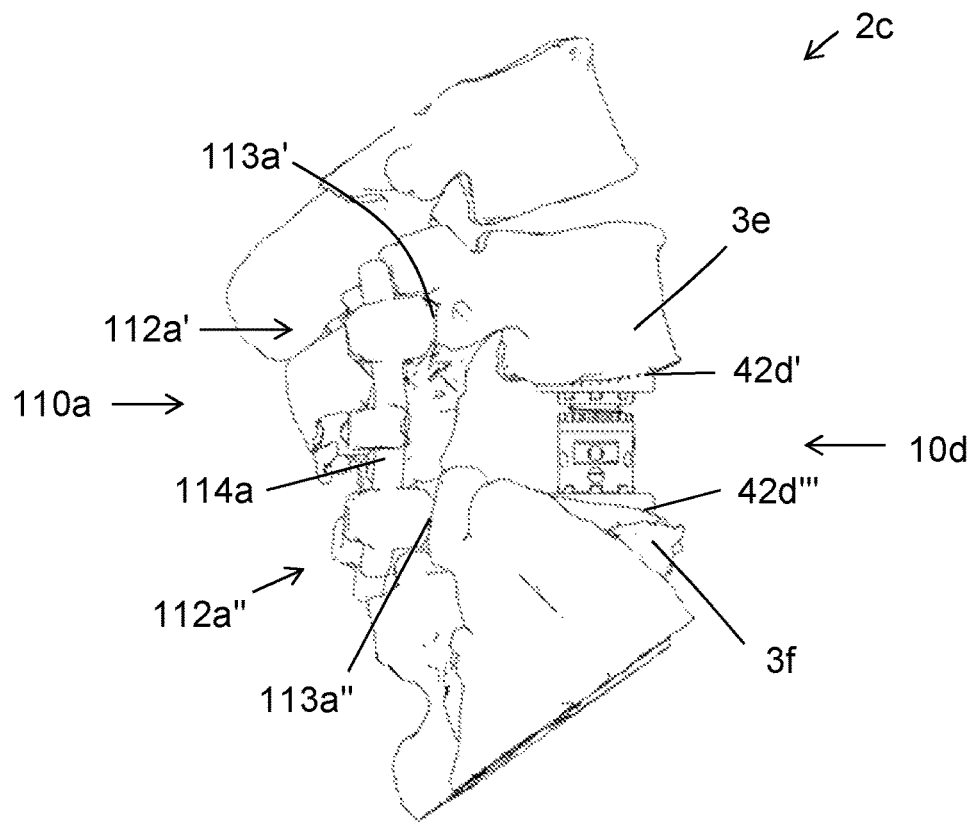
FIG. 13 illustrates a side view of the expandable cage, shown in FIG. 10, providing support to a spine with the assistance of posterior pedicle screws and rods.

The component-engaging part 60d is shown further in FIGS. 12 and 13. The component-engaging part 60d includes a body 62d, a rotating portion 64d and a (linear) movement portion 66d. The rotating portion 64d is configured to allow the components 20d', 20d'' to rotate about the body 62d. This allows the components 20d', 20d'' to find an angle, whether rotating about the axial direction of the body 62d and/or in a sagittal/transverse plane to the axial direction of the body 62d, to suitably engage the discs 3e, 3f of the spine 2c. In addition, the movement portion 66d allows a portion of the component-engaging part 60d to expand and retract in order to establish a suitable distance between the vertebral endplates 3e, 3f. The movement portion 66d may be adjusted via, for example, a screw. Accordingly, the components 20d', 20d'' can be adjusted between the vertebral endplates 3e, 3f to find suitably engagement therewith.

As also shown in FIG. 13, the implantable medical device 10d may form part of a system. This system may further include a fixation assembly 110a including screws 112a', 112a'' and rods 114a. In this embodiment, the fixation system 110a is located on an opposite side of the spine 2a compared to the implantable medical device 10d. Based on the present invention, it will be appreciated that the screws 112a', 112a" may include a component that provides a surface that suitably matches part of the vertebrae 3e, 3f it is designed to engage with. Once the screws 112a', 112a" are in place, the rod 114a can be connected therebetween to assist in fixing movement of the spine.

Figure 16:
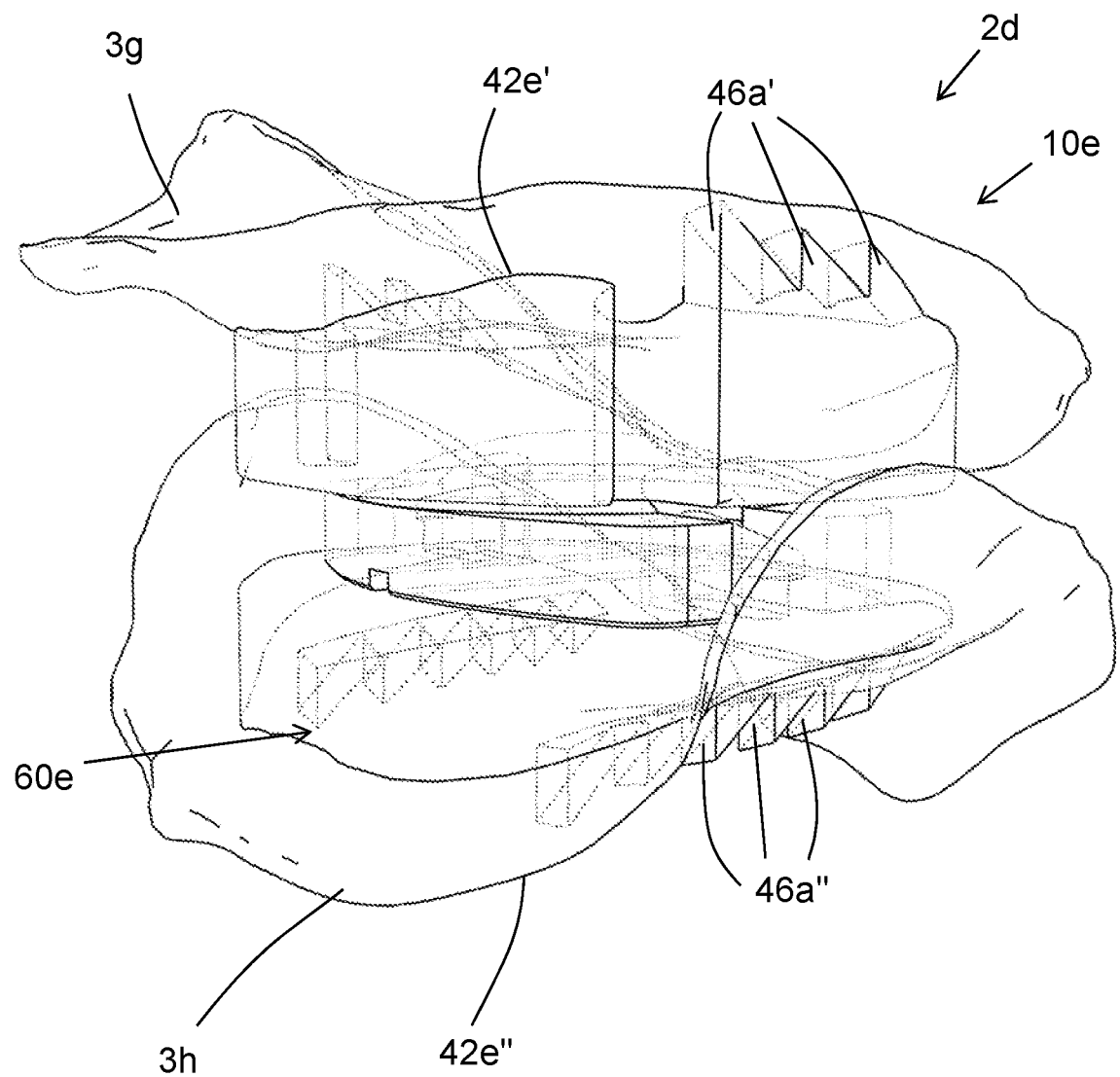
FIG. 16 illustrates a perspective view of the disc replacement device, according to an embodiment of the invention.

As further appreciated below, mechanical disc replacement devices can broadly be classified into two groups: i) biasing based mid-section devices (i.e. springs/elastomers); and ii) floating block mid-section devices. FIG. 14 illustrates a front view of two cervical vertebrae 3g, 3h, as in their planned post-operative position, for an implantable medical device 10e in the form of a disc replacement mechanism. The vertebral endplate surfaces of the vertebrae 3g, 3h include contours. A triangulated mesh is used to model the surfaces that correspond to the surfaces 40e', 40e" in FIG. 14. FIG. 15 shows a subsequent model of the component 10e, which is a floating block mid-section disc replacement device type. The device 10e further includes a plurality of protrusions in the form of teeth 46a', 46a" that are configured to pierce respective vertebral endplates of the vertebrae 3g, 3h. This is shown further in FIG. 16 where the teeth 46a', 46a" are shown to have punctured through the bone surface of the vertebrae 3g, 3h.

The device 10e also includes a component-engaging part 60e that is in the form of a floating component. The floating component is an off-the-shelf product that is configured to connect with the components 20e', 20e". The floating of the component-engaging part 60e allows for suitable movement between the vertebral bodies 3g, 3h. In this regard, the matching of the contours in surfaces 42e', 42e" to the anatomical contours of the vertebral endplates of the vertebrae 3g, 3h permit components 20e', 20e" to be customised. This reduces the need for surgical preparation, meaning that less bone is removed to fit the device 10e, as well as increasing the contact surface area of the device 10e with the anatomy. Leaving the bone substantially intact assists in: i) reducing the chance of subsidence of the device 10e into the vertebral body; and ii) increasing the force needed for the teeth to pull out through the bone.

Figure 17:
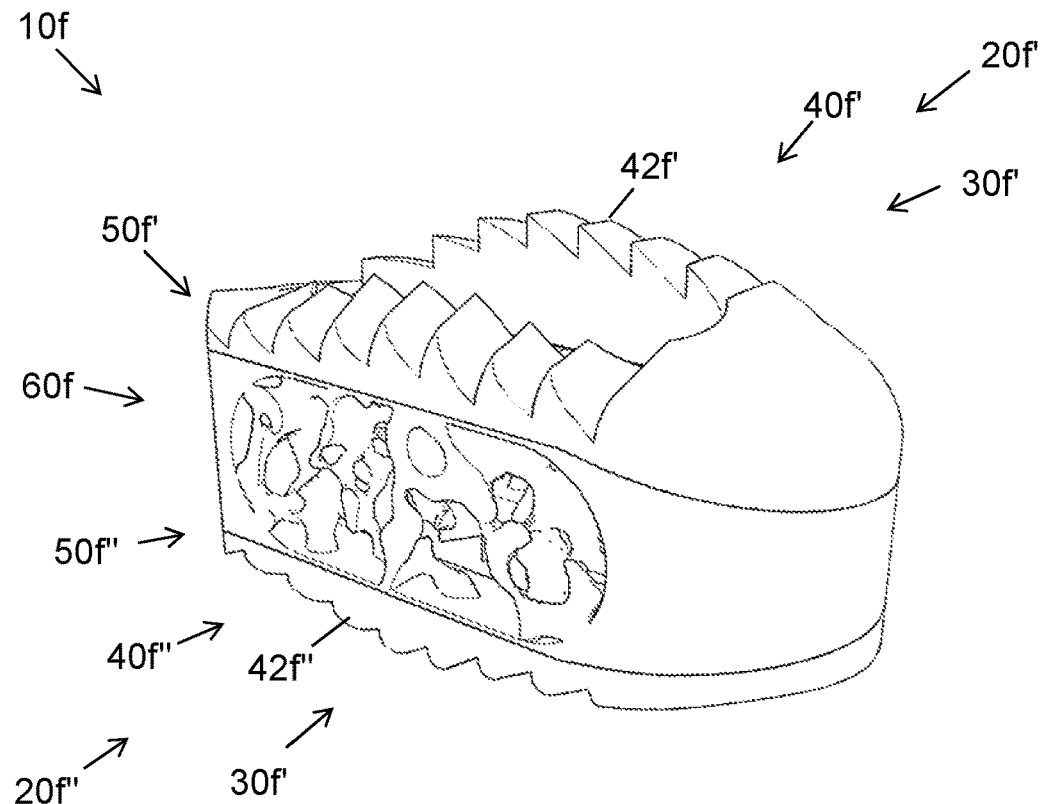
FIG. 17 illustrates a perspective view of an implantable medical device in the form of a (Posterior Lumbar Interbody Fusion, or PLIF) cage, according to an embodiment of the invention.

FIG. 17 illustrates an implantable medical device 10f in the form of a posterior lumbar interbody fusion (PLIF) cage. The device 10f acts as a one piece interbody fusion, or spacer, device whilst, for example, the device 10e acts as a floating block mid-section disc replacement device. The device 10f includes components 20f', 20f" on either side of the component-engaging part 60f. The components 20f', 20f" are connected in an integral manner to the component-engaging part 60f. This is in contrast to the embodiments above where the other components 20 typically retain separable bodies after being secured. The component-engaging part 60f includes a lattice geometry that remains constant when different components 20f', 20f" are associated therewith.

Figure 18:
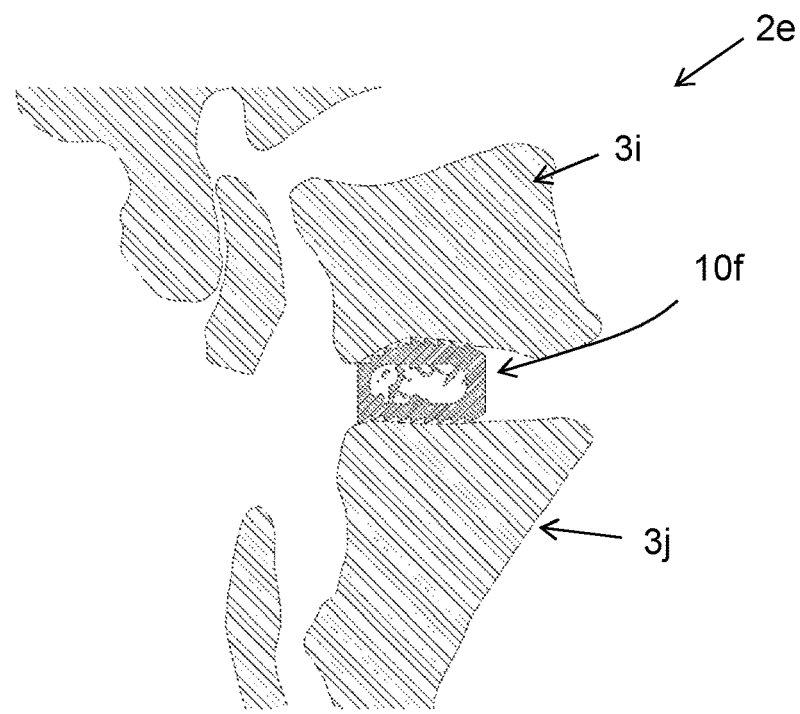
FIG. 18 illustrates a side view of the cage, shown in FIG. 17, implanted into a spine.

The components 20f', 20f" include respective bodies 30f', 30f" that have surfaces 40f', 40f" with contours 42f', 42f" configured to match and engage with vertebral bodies 3i, 3j of the spine 2e. This is shown further in FIG. 18. The components 20f', 20f" includes part engaging surfaces 50f', 50f" that suitably connect with the portion of the component-engaging part 60f.

Figure 19:
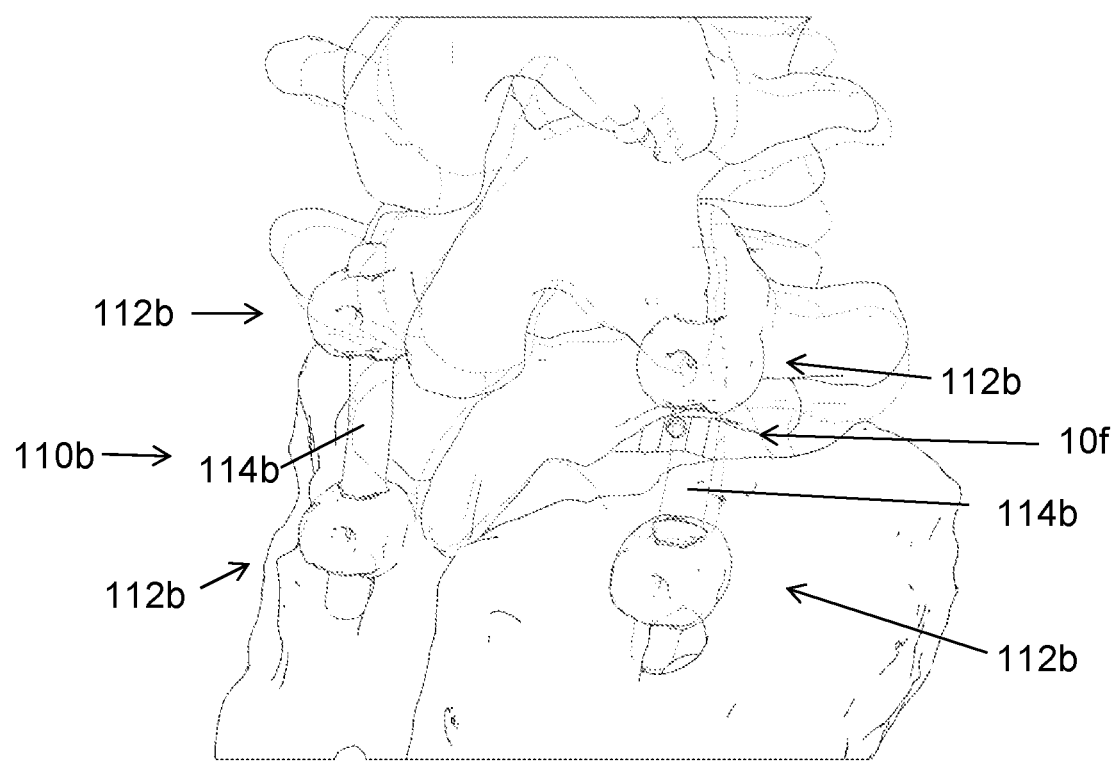
FIG. 19 illustrates a rear perspective view of a spine using pedicle screws and rods, along with the cage show in FIG. 17, to stabilise the spine.

As shown further in FIG. 19, and in a similar manner to FIG. 13, the implantable medical device 10f may form part of a system. In this embodiment, this system includes a fixation assembly 110b having screws 112b', 112b" and rods 114b. Once the screws 112b', 112b" are in place, the rod 114b can be connected therebetween to assist in fixing movement of the spine. In this regard, the combination of the device 10f, screws 112b', 112b" and rods 114b provide a solution for positioning the spine 2e to ultimately improve patient comfort.

With the above in mind, inserting the implantable medical devices 10 into a patient requires retrieving the components 20. Potentially, a number of component engaging parts 60 may be on hand and, through a process of elimination, it can be determined which component engaging part 60 will restore the patient's anatomy in the appropriate manner. Furthermore, the component parts 20 may be interchanged to find a suitable combination. Once the components 20 and engaging part 60 is selected, they are secured together. In the present embodiments, the connection between the components 20 and the component-engaging part 60 relies on a frictional arrangement including a click-in mechanism. In further embodiment, it would be appreciated that the components 20 may be fastened to the component-engaging parts 60.

Once the component(s) 20 are secured to the component-engaging part 60, the device 10 is implanted into the patient. During this process, the component-engaging part 60 may be adjusted to allow the component(s) 20 to suitably engage the bone or joint surface. For example, the rotating portion 64d of the component-engaging part 60d may be rotated, from a first position to a second position, in order achieve a required angle/height for the surfaces 40 of the component (s) 20 to substantially engage and complement the bone or joint surface. Similarly, the movement portion 66d may be shifted, in a substantially longitudinal direction, to allow engagement with the associated surfaces of the vertebrae 3.

The implantable medical devices 10 provide a personalised device that can be manufactured and provided at a reduced cost, due to the use of (generic) component-engaging parts 60, whilst maintaining the benefits of personalised devices in terms of device-anatomy fit. Due to the common interface between the components 20 and the component-engaging parts 60, there is the potential to swap the (generic) component-engaging parts 60 at the time of surgery. Furthermore, different components 20 may be on hand allowing for other suitable combinations. This gives, for example, surgeons much more flexibility in treatment options. By way of example, if a different amount of height/angle is required for ALIF device 60b, the surgeon can choose from a number of other component-engaging parts 60 that can assist in providing a suitable solution (as shown in FIG. 8). In other words, the implantable medical devices 10 give surgeons more flexibility over some critical dimensions. This assists in avoiding problems where: i) anatomy has changed between medical imaging and surgery; or ii) the anatomy changes during the procedure.

Furthermore, the implantable medical devices 10 assist in reducing the amount of metal alloys implanted into a patient's body as any, or all, parts of the device 10 can be made out of non-metallic materials (e.g. polymers, organic tissues). This reduces the potential adverse immune-response and rejection of the device 10. Moreover, post scanning of the device, potentially with CT and/or MRI scans, is more readily available and other forms of therapy become possible (e.g. beam therapies for some cancer patients). The use of different (non-metallic) materials also allows the modulus of the device 10 to be varied to suit a patient's needs. For example, a reduced overall stiffness of the assembled device can be used for a patient with reduced bone density to help prevent the onset of subsidence of the device into the adjacent bone anatomy.

The implantable medical devices 10 also reduce the volume of 3D printed material that is needed to produce a personalised medical device, which reduces the cost per unit of personalised devices as 3D printing manufacturing costs are based on the volume of material to be manufactured. Accordingly, the embodiments of the present invention reduce the overall cost of producing personalised devices as the 'generic' part 60 of the device 10 can be mass produced using traditional manufacturing methods (which take advantage of 'economy-of-scale' production). The embodiments of the present disclosure also reduce the number of personalised components 20 that need to be supplied for the treatment of each patient, obviating the need to manufacture multiple devices for a single patient and thereby reducing the costs and waste associated with production of patient specific devices.

In addition, it would be appreciated that the present invention has a range of medical applications. For example, in a dental application, a patent specific crown, designed to complement opposing teeth, may be attached with a generic part which is designed to be embedded in a mandibular bone. Further, it is to be understood that the present invention is also applicable to other total joint replacement devices whose design consists of a floating mid-section and anatomy interfacing sections. Such devices effectively include devices designed for any other synovial joint where arthroplasty is suitable including, but not limited to: total facet replacement/arthroplasty (spine); total knee arthroplasty; total hip arthroplasty; total ankle arthroplasty; 're-surfacing' hip and knee arthroplasty; and total/partial shoulder and elbow arthroplasty.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step etc.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

The invention claimed is:

1. A corpectomy fusion component including:
   a body having one or more surfaces with a contour formed to be substantially complementary to an anatomical surface of a specific patient;
   the body adapted to securably engage with a component-engaging part such that the component-engaging part is configured to adjust from a first position to a second position, in a substantially linearly direction in order to adjust the height at least part of an implantable medical device,
   wherein:
      the one or more surfaces are substantially configured to evenly engage with the anatomical surface of the specific patient when the component is secured to the component-engaging part and the implantable medical device implanted in the patient; and
      the body is at least in part manufactured by additive manufacturing.

2. The corpectomy fusion component of claim 1, wherein the anatomical surface is a specific anatomical surface unique to the specific patient such that the one or more surfaces have been explicitly designed for the specific patient.

3. The corpectomy fusion component of claim 1, wherein the one or more surfaces are manufactured by additive manufacturing for the specific patient such that at least part of the one or more surfaces will not evenly engage a separate patient.

4. The corpectomy fusion component of claim 1, wherein the anatomical surface is taken in-situ within a human or animal patient.

5. The corpectomy fusion component of claim 1, wherein the one or more surfaces are custom manufactured to be complementary to the anatomical surface of the specific patient based on a scan of the anatomical surface of the specific patient.

6. The corpectomy fusion component of claim 1, wherein the body includes a part engaging surface that is located on an opposite side of the body to the one or more surfaces.

7. The corpectomy fusion component of claim 1, wherein the body has a set of teeth to further securely engage with the anatomical surface by being able to puncture therethrough.

8. The corpectomy fusion component of claim 1, wherein the additive manufacturing is in the form of 3D printing.

9. The implantable medical device of claim 1, wherein the body is contoured such that the body is convex in some regions and concave in other regions and the body is configured to engage complimentary concave and convex portions, respectively, of the anatomical surface of the specific patient.

10. The corpectomy fusion component of claim 1, wherein:
    the anatomical surface is a unique anatomical surface of the specific patient; and
    the contour is unique such that the one or more surfaces uniquely correspond to the unique anatomical surface.

11. An implantable medical device including:
    a corpectomy fusion component having a body with one or more surfaces that have a contour that is substantially complementary to an anatomical surface of a specific patient; and
    a component-engaging part that is adapted to securably engage with the component,
    wherein:
       the one or more surfaces are substantially configured to evenly engage with the anatomical surface of the specific patient when the corpectomy fusion component is secured to the component-engaging part and the medical device implanted in the patient to stabilize a spine after vertebral body removal;

the body is at least in part manufactured by additive manufacturing; and the component-engaging part is configured to adjust from a first position to a second position in a substantially linear direction in order to adjust a height of the implantable medical device.

12. The implantable medical device of claim 11, wherein the component-engaging part is configured to be useable for a number of patients whilst the component has been explicitly designed for the specific patient.

13. The implantable medical device of claim 11, wherein the component-engaging part is adapted to move from a connected position with the component to a released position.

14. The implantable medical device of claim 11, wherein the corpectomy fusion component is a first corpectomy component, the implantable medical device further comprising:

a second corpectomy fusion component having a body with one or more surfaces comprising a contour that is substantially complementary to a separate anatomical surface of the specific patient is securably engaged with the component-engaging part.

15. The corpectomy fusion component of claim 11, wherein the body is contoured such that the body is convex in some regions and concave in other regions and the body is configured to engage complimentary concave and convex portions, respectively, of the anatomical surface of the specific patient.

16. The implantable medical device of claim 11, wherein:
the anatomical surface is a unique anatomical surface of the specific patient; and
the contour is unique such that the one or more surfaces uniquely correspond to the unique anatomical surface.

17. The implantable medical device of claim 11, wherein the corpectomy fusion component is formed from a different material compared to the component-engaging part.

18. The implantable medical device of claim 11, wherein the component-engaging part includes a screw and adjusting the screw allows the component-engaging part to shift from a fixed configuration to a moving configuration.

19. A method for implanting a medical device, the method comprising:

retrieving a corpectomy fusion component having a body with one or more surfaces that have a contour substantially complementary to an anatomical surface of a specific patient;

securing the corpectomy fusion component to a component-engaging part to form at least part of the medical device; and implanting the medical device into the specific patient such that the one or more surfaces substantially engage with the anatomical surface of the specific patient to stabilize a spine after vertebral body removal, implanting the medical device including adjusting at least a portion of the component-engaging part, relative to another portion of the component-engaging part, from a first position to a second position in a in a substantially linear direction to adjust a height of the medical device;

wherein the body is at least in part manufactured by additive manufacturing.

20. The method of claim 19, further comprising:
modeling the anatomical surface of the specific patient based on an anatomical scan of the specific patient; and
defining a triangulated point surface of the one or more surfaces based on the anatomical scan; and
additively manufacturing the component, the contour of the one or more surfaces manufactured based on the triangular point surface.

21. The method of claim 19, wherein securing the component to the component-engaging part includes retrieving a number of component-engaging parts to determine which one would allow the one or more surfaces to substantially complement the anatomical surface of the specific patient.

22. The method of claim 19, wherein the step of securing the component to the component-engaging part includes fastening the component to the component-engaging part.

23. The method of claim 19, further comprising:
imaging the anatomical surface of the patient to produce a three-dimensional scan of the anatomical surface; and
additively manufacturing the body based on the three-dimensional scan such that the contour models and is substantially complementary to the anatomical surface of the specific patient.

24. The method of claim 19, wherein the contour is nonlinear and is configured to engage a complimentary non-linear portion of the anatomical surface.

25. The method of claim 14, further comprising fastening a screw to fix the height of the medical device after adjusting the height of the medical device.

* * * * *

UNITED STATES PATENT AND TRADEMARK OFFICE
CERTIFICATE OF CORRECTION

| | | |
|---|---|---|
| PATENT NO. | : 12,226,318 B2 | Page 1 of 1 |
| APPLICATION NO. | : 17/311252 | |
| DATED | : February 18, 2025 | |
| INVENTOR(S) | : William Chase Harrington Parr et al. | |

It is certified that error appears in the above-identified patent and that said Letters Patent is hereby corrected as shown below:

In the Claims

Column 14, Claim 9, Line 42:
"The implantable medical device"
Should read:
--The corpectomy fusion component--

Column 15, Claim 15, Line 23:
"The corpectomy fusion component"
Should read:
--The implantable medical device--

Column 16, Claim 25, Line 43:
"claim 14"
Should read:
--claim 19--

Signed and Sealed this
Twenty-second Day of April, 2025

Coke Morgan Stewart
*Acting Director of the United States Patent and Trademark Office*